(12) United States Patent
Butts et al.

(10) Patent No.: US 6,390,102 B1
(45) Date of Patent: May 21, 2002

(54) SILICONE COMPOSITIONS FOR PERSONAL CARE PRODUCTS AND METHOD FOR MAKING

(75) Inventors: Matthew David Butts, Rexford; Susan Adams Nye, Feura Bush; Christopher Michael Byrne, Clifton Park, all of NY (US); Peter Marte Torgerson, Washington Court House, OH (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/616,534

(22) Filed: Jul. 14, 2000

(51) Int. Cl.$^7$ .............................. A61K 7/08; C08G 77/26
(52) U.S. Cl. .......................... 132/202; 528/38; 528/30; 528/31; 528/33; 528/27; 424/70.12; 525/474; 523/105
(58) Field of Search ................................ 528/38, 30, 31, 528/33, 27; 424/70.12; 525/474; 523/105; 132/202

(56) References Cited

U.S. PATENT DOCUMENTS

| | | |
|---|---|---|
| 4,567,039 A | 1/1986 | Stadnick et al. |
| 4,820,308 A | 4/1989 | Madrange et al. |
| 4,859,460 A | 8/1989 | Mahieu et al. |
| 4,971,786 A | 11/1990 | Grollier et al. |
| 4,973,475 A | 11/1990 | Schnetzinger et al. |
| 5,030,756 A | 7/1991 | Deppert et al. |
| 5,087,733 A | 2/1992 | Deppert et al. |
| 5,160,733 A | 11/1992 | Berthiaume |
| 5,206,013 A | 4/1993 | Deppert et al. |
| 5,211,942 A | 5/1993 | Deppert et al. |
| 5,254,335 A | 10/1993 | Deppert et al. |
| 5,280,099 A | 1/1994 | Imperante et al. |
| 5,326,890 A | 7/1994 | Wnek et al. |
| 5,350,572 A | 9/1994 | Savaides et al. |
| 5,523,080 A | 6/1996 | Gough et al. |
| 5,525,332 A | 6/1996 | Gough et al. |
| 5,609,856 A | 3/1997 | Dubief et al. |
| 5,609,861 A | 3/1997 | Dubief et al. |
| 5,969,077 A | 10/1999 | Schrock et al. |

FOREIGN PATENT DOCUMENTS

| | | |
|---|---|---|
| EP | 0159628 | 4/1985 |
| EP | 0509922 | 4/1992 |
| WO | 9632432 | 10/1996 |
| WO | 9935180 | 12/1997 |
| WO | 9838974 | 4/1998 |
| WO | 0040210 | 1/2000 |

OTHER PUBLICATIONS

"Development of Novel Attachable Initiator for "Living" radical Polymerization and Synthesis of Polysiloxane Block Copolymer", Nakagawa and Matyjaszewski, Amer. Chem. Soc., Polym. Preprints 1996, 270–271.

*Primary Examiner*—Robert Dawson
*Assistant Examiner*—Kuo-Liang Peng
(74) *Attorney, Agent, or Firm*—Bernadette M. Bennett; Noreen C. Johnson

(57) ABSTRACT

A composition and method for making a silicone composition is provided which comprises at least one polysiloxane or silicone resin containing at least one linker and either one or two molecular hooks.

44 Claims, No Drawings

SILICONE COMPOSITIONS FOR PERSONAL CARE PRODUCTS AND METHOD FOR MAKING

BACKGROUND OF THE INVENTION

The present invention relates to compositions for personal care products. More particularly, the present invention relates to silicone compositions which achieve conditioning benefits in hair care products.

Silicones are widely used in hair care products due to the conditioning benefit that they impart to hair. By modern day technology, the silicone is deposited on hair during the application process but is held only by weak physical forces, such as hydrogen bonding or van der Waals interactions. Because the interactive forces are weak, the benefits of silicone by deposition are short lived. Generally, conditioning benefits are attributed to the deposition of high molecular weight, high viscosity fluids and gums which can weigh down the hair. Buildup of silicone compositions is an issue in hair care, and it is perceived by consumers to be a serious negative. Beneficial conditioning effects can also be caused by treating hair with silanol capped amino-functionalized silicones. These can undergo condensation cure reactions on hair to form somewhat durable films. Buildup is still a concern upon repeated applications.

It is widely known by those skilled in the art that covalent bonding is one key to "permanent" hair treatment. Processes which alter the structure of the hair, such as permanent wave and color treatment methods, do provide longer lasting effects. These processes include glycolate reduction and peroxide reoxidation. A significant disadvantage of these processes is that they are very damaging to hair and can only be carried out infrequently.

Gough et al. in U.S. Pat. Nos. 5,523,080 and 5,525,332 describe the synthesis of silicone-azlactone polymers which exhibit covalent bonding and "permanent" conditioning benefit. Gough et al. discuss incorporating an azlactone-functionalized copolymer which consists of vinylazlactone and methacryloyl polydimethylsiloxane monomers into a silicone-active group-hair structure. The hair treatment using the silicone-azlactone polymers does not consist of the steps of reduction with a glycolate or reoxidation with peroxide.

It is desirable to produce silicone compositions which can be used to treat damaged hair and provide durable benefits. Thus, silicone products are constantly being sought which can both covalently bond to hair as well as impart hair care benefits appreciated by consumers.

BRIEF SUMMARY OF THE INVENTION

The present invention provides a silicone composition which comprises at least one polysiloxane or silicone resin containing at least one linker, and either one or two molecular hooks.

The present invention further provides a method for making a silicone composition comprising at least one polysiloxane or silicone resin, at least one linker, and in a range between one and two molecular hooks, which method comprises combining a linker with a molecular hook and a polysiloxane or silicone resin.

DETAILED DESCRIPTION OF THE INVENTION

The present invention includes a silicone composition which includes at least one polysiloxane or silicone resin containing at least one linker, and either one or two molecular hooks. When the molecular hooks are present in a range between 1 and 2, there is significantly less buildup than when hair is treated repeatedly with formulations containing greater than two molecular hooks. "Significantly less buildup" as used herein refers to a measurably lesser amount of silicone deposited on hair as a result of repeat applications, as determined by x-ray fluorescence, when the silicone composition comprises between 1 and 2 molecular hooks versus greater than 2 molecular hooks.

The linker is bound to both a molecular hook and to an atom of a polysiloxane or silicone resin. Preferably the linker is bound to a polysiloxane or silicone resin through a silicon (Si), carbon (C), oxygen (O), nitrogen (N), or sulfur (S) atom, and most preferably through a silicon atom. When more than one linker is present, it is also contemplated that linkers may be bound to a polysiloxane or silicone resin through more than one type of atom, for example through both silicon and carbon atoms.

The present invention includes a silicone composition having the formula:

where the subscripts a, b, c, d, e, f and g are zero or a positive integer, subject to the limitation that the sum of the subscripts b, d and f is one or two; where M has the formula:

M' has the formula:

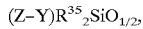

D has the formula:

D' has the formula:

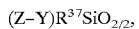

T has the formula:

T' has the formula:

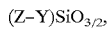

and Q has the formula $SiO_{4/2}$, where each $R^{34}$, $R^{35}$, $R^{36}$, $R^{37}$, $R^{38}$ is independently at each occurrence a hydrogen atom, $C_{1-22}$ alkyl, $C_{1-22}$ alkoxy, $C_{2-22}$ alkenyl, $C_{6-14}$ aryl, $C_{6-22}$ alkyl-substituted aryl, or $C_{6-22}$ aralkyl which groups may be halogenated, for example, fluorinated to contain fluorocarbons such as $C_{1-22}$ fluoroalkyl, or may contain amino groups to form aminoalkyls, for example aminopropyl or aminoethylaminopropyl, or may contain polyether units of the formula $(CH_2CHR^{40}O)_k$ where $R^{40}$ is $CH_3$ or H and "k" is in a range between about 4 and about 20; Z, independently at each occurrence, represents a molecular hook; and Y, independently at each occurrence, represents a linker. The term "alkyl" as used in various embodiments of the present invention is intended to designate both normal alkyl, branched alkyl, aralkyl, and cycloalkyl radicals. Normal and branched alkyl radicals are preferably those containing in a range between about 1 and about 12 carbon atoms, and include as illustrative non-limiting examples methyl, ethyl, propyl, isopropyl, butyl, tertiary-butyl, pentyl, neopentyl, and hexyl. Cycloalkyl radicals represented are preferably those containing in a range between about 4 and about 12 ring carbon atoms. Some illustrative non-limiting examples of these cycloalkyl radicals include cyclobutyl, cyclopentyl, cyclohexyl, methylcyclohexyl, and cycloheptyl. Preferred aralkyl radicals are those containing in a range between about 7 and about 14 carbon atoms; these include, but are not limited to, benzyl, phenylbutyl, phenylpropyl, and phenylethyl. Aryl radicals used in the various embodiments of the present invention are preferably those containing in a range between about 6 and about 14 ring carbon atoms. Some illustrative non-limiting examples of these aryl radicals include phenyl, biphenyl, and naphthyl. An illustrative non-limiting example of a halogenated moiety suitable is trifluoropropyl.

The polysiloxanes or silicone resins of the present invention are typically prepared by the hydrosilylation of an organohydrogen silicone having the formula:

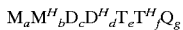

where the subscripts a, b, c, d, e, f and g are zero or a positive integer, subject to the limitation that the sum of the subscripts b, d and f is one or greater; M, D, T and Q are defined as above;

$M^H$ has the formula:

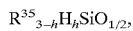

$D^H$ has the formula:

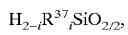

$T^H$ has the formula:

where each $R^{35}$ and $R^{37}$ is independently as defined above; subscript h is in a range between 1 and 3; and subscript i is 0 or 1.

Hydrosilylation is typically accomplished in the presence of a suitable hydrosilylation catalyst. The catalysts preferred for use with these compositions are described in U.S. Pat. Nos. 3,715,334; 3,775,452; and 3,814,730 to Karstedt. Additional background concerning the art may be found at J. L. Spier, "Homogeneous Catalysis of Hydrosilation by Transition Metals, in *Advances in Organometallic Chemistry*, volume 17, pages 407 through 447, F. G. A. Stone and R. West editors, published by the Academic Press (New York, 1979). A preferred catalyst contains platinum. Persons skilled in the art can easily determine an effective amount of platinum catalyst. Generally, an effective amount is in a range between about 0.1 parts per million and about 50 parts per million of the total silicone composition.

The organohydrogen silicone compounds that are the precursors to the compounds of the present invention may be prepared by the process disclosed in U.S. Pat. No. 5,420,221. The '221 patent discloses the redistribution of polydimethylsiloxane polymers with organohydrogen silicone polymers and optionally, added chain stopper, to provide a silicone with randomly-distributed hydride groups using a Lewis acid catalyst, preferably a phosphonitrilic compound.

Synthesis of the polysiloxane or silicone resin may also be performed by other methods known to those skilled in the art, for example, the hydrosilylation of a monomer such as methyldichlorosilane could be followed by co-hydrolysis with the appropriate dialkyldichlorosilane and optionally, chlorotrimethylsilane.

It is to be noted that as pure compounds, the subscripts describing the organohydrogen siloxane precursor and the hydrosilylation adduct of the present invention are integers as required by the rules of chemical stoichiometry. The subscripts will assume non-integral values for mixtures of compounds that are described by these formulas. The restrictions on the subscripts heretofore described for the stoichiometric subscripts of these compounds are for the pure compounds, not the mixtures.

In specific embodiments of the present invention, the silicone composition typically comprises at least one compound of the following formulas, (I), (II), (III), (IV), (V), or (VI):

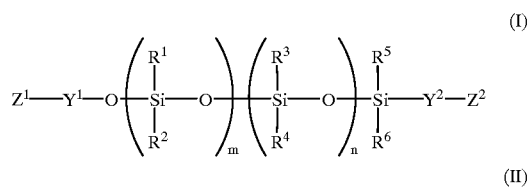

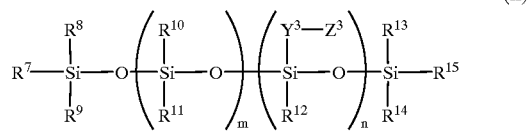

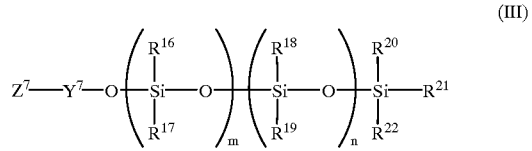

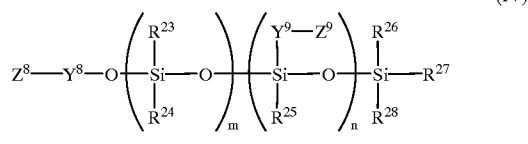

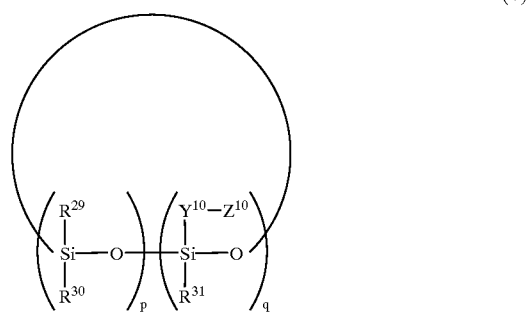

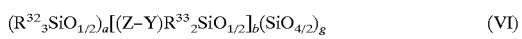

where each $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, and $R^{33}$ is independently at each occurrence a hydrogen atom, $C_{1-22}$ alkyl, $C_{1-22}$ alkoxy, $C_{2-22}$ alkenyl, $C_{6-14}$ aryl, $C_{6-22}$ alkyl-substituted aryl, or $C_{6-22}$ aralkyl which groups may be halogenated, for example, fluorinated to contain fluorocarbons, may contain amino groups to form aminoalkyls, or may contain polyether units; Z, $Z^{1-3}$, and $Z^{7-10}$, independently at each occurrence, represents a molecular hook; and Y, $Y^{1-3}$ and, and $Y^{7-10}$, independently at each occurrence, represents a linker; wherein "m" in each formula has a value in a range between about 0 and about 26,000, preferably about 0 and about 1000, more preferably between about 1 and about 250, still more preferably between about 3 and about 250, even more preferably between about 5 and about 150, and most preferably between about 15 and about 120; "n" in each formula has a value in a range between about 0 and about 2 with the proviso that in formula (II) "n" is not 0; "m+n" in each formula has a value in a range between about 1 and about 26,000, preferably in a range between about 3 and about 250, more preferably between about 5 to about 150, and most preferably between about 15 and about 120; "q" has a value of 1 or 2; "p+q" has a value of at least 3, preferably in a range between about 3 and about 20, more preferably in a range between about 3 and about 10, and most preferably in a range between about 3 and 6; "a" has a value greater than or equal to one; and "b" and "g" have a value of at least one. $R^{1-33}$ is preferably methyl. The preferred silicone composition includes a compound of the formula (I) or (II). The polysiloxane or silicone resin typically has a molecular weight in a range between about 100 and about 2,000,000, preferably in a range between about 250 and about 50,000, more preferably in a range between about 500 and about 25,000, and most preferably in a range between about 500 and about 15,000.

In one embodiment of the present invention a polysiloxane- or silicone resin-containing composition includes a preponderance of a specific linear, branched, cross-linked, or cyclic polysiloxane or silicone resin. In other embodiments of the present invention, a polysiloxane- or silicone resin-containing composition comprises a mixture of polysiloxanes, mixture of silicone resins, or mixtures of polysiloxanes and silicone resins which may include linear, branched, cross-linked, and cyclic species. Also, suitable compositions may comprise one or more polysiloxanes, silicone resins, and mixtures thereof which may contain adventitious amounts of other species, for example, arising during the synthesis process for said polysiloxanes or silicone resins, for example at a level in a range between about 0.0001 wt. % and about 5 wt. % based on total silicon-containing species. In illustrative examples, suitable compositions may contain adventitious amounts of $D_4$, or species containing Si—H, Si—OH, Si—O— alkyl bonds, and mixtures thereof.

The molecular hook may be selected from the range consisting of heterocyclic molecular hooks, $sp^2$ aliphatic trigonal carbon molecular hooks, $sp^3$ carbon molecular hooks, metal based molecular hooks, non-metal and metalloid based molecular hooks, energy-sensitive molecular hooks and mixtures thereof. The molecular hook is preferably selected from the range consisting of heterocyclic molecular hooks, $sp^2$ aliphatic trigonal carbon molecular hooks, $sp^3$ carbon molecular hooks and non-metal molecular hooks. The molecular hook is more preferably selected from heterocyclic molecular hooks, $sp^2$ aliphatic trigonal carbon molecular hooks and non-metal molecular hooks.

The molecular hook of the present invention preferably comprises a sulfur-containing compound wherein the sulfur-containing protective group may be a heterocyclic ring or ring system. Heterocyclic groups that are suitable for use in the present invention include mono- or polyunsaturated or saturated heterocyclic rings, heterocyclic ring systems, fused heterocyclic ring systems, substituted heterocyclic rings, substituted heterocyclic ring systems or substituted fused heterocyclic ring systems. The heterocyclic rings contain in a range between about three and about thirty members, and may contain electronegative heteroatoms including N, O, S, or P. The heterocyclic rings or ring systems also may contain exocyclic double bonds of the C=M type wherein M is O, S, $NE^1$ or $CE^1E^2$. $E^1$ and $E^2$ used here, and E, $E^3$, and $E^4$ used hereinafter, each represent, independently from one another, a monovalent group which can be a silicone group, H or any of the following: a straight, branched or mono- or polycyclic aliphatic, mono or polyunsaturated alkyl, aryl, heteroalkyl, heteroaliphatic or heteroolefinic system including carbon atoms in a range between about 1 and about 30 together with heteroatoms in a range between about 0 and about 15, especially O, N, S, P, Si, and can incorporate one or more substituents including, but not limited to, mono, poly or perfluoro substitution.

In particular, the molecular hook may be a heterocyclic pyridinium compound (VII), a heterocyclic triazinium compound (VIII), a heterocyclic pyrimidinium compound (IX), or a heterocyclic pyrazine compound (X):

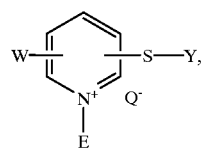

(VII)

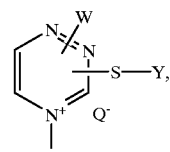

(VIII)

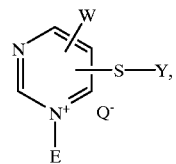

(IX)

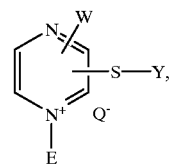

(X)

wherein W represents optional substituents on the heterocyclic ring or ring system, Y represents the linker, $Q^-$ represents a counterion, and E is defined above. The preferred molecular hook is the pyrimidinium molecular hook of formula (IX).

Optional substituents, W, which can be present on the heterocyclic ring or ring system can be selected from electron withdrawing, electron neutral, or electron donating groups with Hammett sigma para values between −1.0 and +1.5 comprising carbon-linked groups of the classes defined as $E^1$, $E^2$, $E^3$, and $E^4$; S-linked groups including $SE^1$, SCN, $SO_2E^1$, $SO_3E^1$, $SSE^1$, $SOE^1$, $SO_2NE^1E^2$, $SNE^1E^2$, $S(NE^1)E^2$, $SE^1(NE^2)$, $SONE^1E^2$; O-linked groups including $OE^1$, OCN, $ONE^1E^2$; N-linked groups including $NE^1E^2$, $NE^1E^2E^{3+}$, $NE^1OE^2$, $NE^1SE^2$, NCO, NCS, $NO_2$, $N=NE^1$, $N=NOE^1$, $NE^1CN$, $N=C=NE^1$, $NE^1NE^2E^3$, $NE^1NE^2NE^3E^4$, $NE^1N=NE^2$; other miscellaneous groups including $CONE^1_2$, $CONE^1COE^2$, $C(=NE^1)NE^1E^2$, CHO, CHS, CN, NC, Hal, and derived groups that connect one or more of the optional substituents via a ring system; Hal is fluorine, chlorine, bromine, or iodine. E, $E^1$, $E^2$, $E^3$, and $E^4$ are defined above. The substituent E is preferably methyl.

The counterion, $Q^-$, can include halides, borates, phosphates, tosylates, mesylates, triflates, and other counterions known to those skilled in the art.

The linker comprises any $C_1–C_{100}$ alkyl, aryl, or alkylaryl group where the $C_{1-100}$ group can be interrupted by or substituted with aromatic groups or aromatic-containing groups. The $C_{1-100}$ group may also contain one or more heteroatoms such as O, N, or S. Furthermore, the $C_{1-100}$ group may be unsubstituted or substituted with heteroatoms such as halogen. Typically, the linker has the formulas (XI) through (XVII)

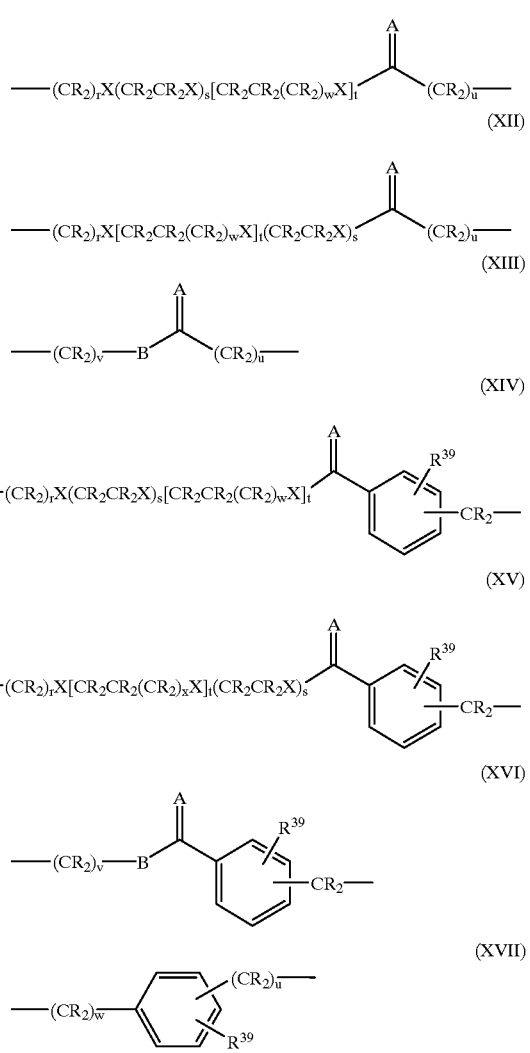

where
r is in a range between about 1 and about 10, preferably 2 or 3;
s is in a range between about 0 and about 100, preferably 4 to 20;
t is in a range between about 0 and about 100, preferably in a range between about 0 and about 20, and most preferably 0;
u is in a range between about 1 and about 10, preferably 1;
v is in a range between about 1 and about 10, preferably 2 or 3;
w is 1 or 2;
x is 1 or 2;
X is O, NOH, NOR or NR, preferably O;
wherein R is independently at each occurrence hydrogen (H), $C_{1-22}$ alkyl, $C_{1-22}$ alkoxy, $C_{2-22}$ alkenyl, $C_{6-14}$ aryl, $C_{6-22}$ alkyl-substituted aryl, or $C_{6-22}$ aralkyl where the can be unsubstituted or substituted with heteroatoms such as oxygen (O), nitrogen (N), sulfur (S) or halogen;
wherein $R^{39}$ is independently at each occurrence hydrogen (H), $C_{1-22}$ alkyl, $C_{1-22}$ alkoxy, $C_{2-22}$ alkenyl, $C_{6-14}$ aryl, $C_{6-22}$ alkyl-substituted aryl, $C_{6-22}$ aralkyl, or fused ring system which may or may not be fused to the phenyl group where the C can be unsubstituted or substituted with heteroatoms such as O, N, S or halogen. $R^{39}$ is preferably H. If $R^{39}$ represents an aryl group, it can be fused to the ring in Formulas (XIII) through (XVI);
A is O, NOH, NOR, NR or S, preferably O;
B is O, NOH, NOR, NR or S, preferably O or NR and most preferably O;
and where the polysiloxane or the silicone resin is bound to the $(CR_2)_r$ (Formula XI, XII, XIV, and XV), $(CR_2)_v$ (Formula XIII and XVI), or $(CR_2)_w$ (Formula XVII). Any of the linker structures shown in Formulas (XI) through (XVII) can also be interupted with cycloaliphatic rings or aromatic rings. Substituents on the phenyl group of formulas (XIV), (XV), (XVI), and (XVII) may be present at any free valence site. The polysiloxane or silicone resin may or may not contain other functionalities by substitution at silicon atoms either the same as or distinct from those bound to the linking groups described above, such as amine-, polyether-, alkyl-, or heteroalkyl-containing groups.

The linker is typically derived from a polysiloxane or silicone resin bound linker precursor which comprises a linker bound to a leaving group. Illustrative leaving groups include halides such as chloride, bromide and iodide; tosylate, mesylate, phosphate; cyclic leaving groups (that is, those in which the leaving group remains bound in the linker) such as epoxy or other cyclic leaving group containing at least one heteroatom; and other leaving groups known to those skilled in the art. Preferred leaving groups are bromide, chloride, and iodide. In synthesis, the leaving group is replaced by a molecular hook, so that the linker becomes bound to a molecular hook.

The method for making the silicone compositions of the present invention includes combining a molecular hook, a polysiloxane or silicone resin, and a linker. The sequence of addition can be varied, for example, the linker and the molecular hook can be combined and this combination can be sequentially combined with a polysiloxane or a silicone resin. Preferably, the linker is combined with a polysiloxane or silicone resin and the combination is sequentially combined with the molecular hook.

Silicone compositions of the present invention which include at least one polysiloxane or silicone resin containing at least one linker, and at least one molecular hook typically impart cosmetic and other durable benefits in products such as hair care products, but also including, textile care products, cosmetic products, oral care products, and animal care products. A particular advantage of the present invention is that many of the described linkers provide solubility, in consumer relevant media, to the silicone composition as well as the potential for additional hair care benefits which may or may not be typically associated with the functional groups of the linker.

The silicone compositions can be delivered to a substrate, for example hair, in any appropriate formulation, for example water or water and alcohol mixtures which can contain in a range between about 1% by weight and about 99% by weight alcohol based on the total formulation.

In order that those skilled in the art will be better able to practice the invention, the following examples are given by way of illustration and not by way of limitation.

In the following examples, $D^{R1}$ through $D^{R4}$ are defined as:

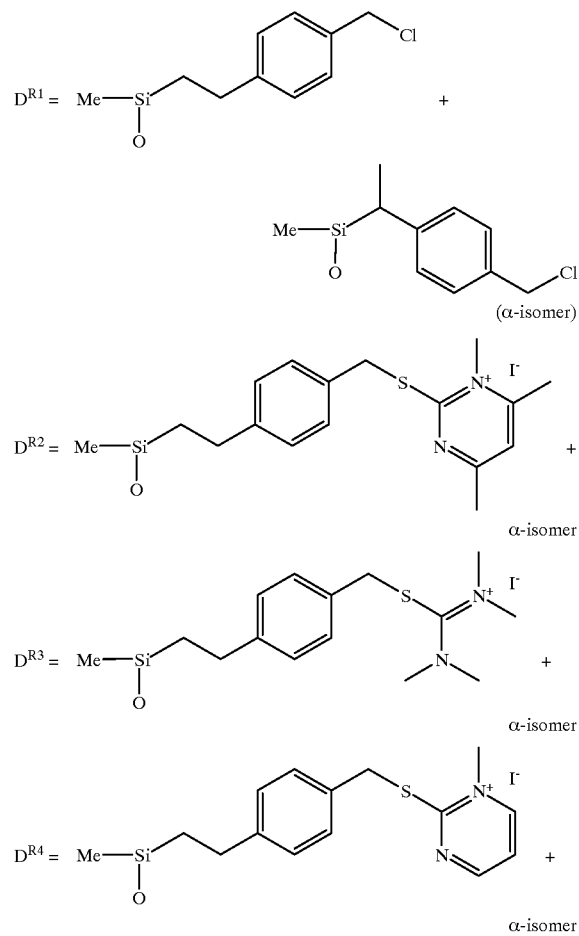

EXAMPLE 1

Silicone hydride fluid ($MD_{48}D^{H}_{3}M$). A 1000 milliliter three-neck round bottom flask equipped with a mechanical stirrer, thermometer attached to a temperature controlling device and a drying tube was charged with a silanol-terminated polydimethylsiloxane polymer (535.1 grams, 7.23 mole dimethylsiloxy groups), a silicone hydride fluid ($MD^{H}_{x}M$, 30.35 grams=0.48 moles methylhydridosiloxy groups +0.019 moles trimethylsiloxy groups), hexamethyl-disiloxane (24.41 grams, 0.3 moles trimethylsiloxy groups) and a linear phosphonitrilo catalyst (2.95 grams of a 2% solution in the silicone hydride fluid, 100 parts per million). The mixture was stirred at 90° C. for two hours after which it was cooled and treated with magnesium oxide (1 gram, 0.0256 moles). The mixture was filtered through Celite to furnish the product as a clear, colorless fluid with viscosity of 58.8 centistokes and hydride level of 828 parts per million. Proton nuclear magnetic resonance spectroscopy ($^{1}$H NMR) (acetone-$d_6$): δ 4.74 (s, 3.0H, SiH), 0.12 (m, 315.0H, $SiCH_3$).

EXAMPLE 2

Benzylchloride-substituted silicone polymer ($MD_{48}D^{R1}_{3}M$). A 5 liter three-neck round bottom flask equipped with a stirbar, thermometer attached to a temperature controlling device, addition funnel and a condenser with a drying tube was charged with the silicone hydride polymer $MD_{48}D^{H}_{3}M$ (931.2 grams, 0.77 moles hydride), 4-vinylbenzyl chloride (7.56 grams, 0.050 moles), di-t-butylphenol (0.52 grams) and Karstedt's catalyst (95.3 milligrams of a 10% Pt solution in $M^{Vi}M^{Vi}$, a GE Silicones product. The mixture was heated to 60° C. and additional 4-vinylbenzyl chloride (110.16 grams, 0.72 moles) was added over 60 minutes with a slight exotherm to 80° C. The reaction was followed by gasiometric hydride analysis and was finished within 6 hours after the addition was complete. The reaction mixture was distilled at 130° C. under vacuum to remove unreacted volatile compounds to provide product with viscosity of 124 centistokes. $^{1}$H NMR (acetone-$d_6$): δ 7.33 (m, 6.0H, phenyl), 7.22 (m, 6.0H, phenyl), 4.66 (s, 6.0H, $CH_2Cl$), 2.73 (m, 6.0H, $SiCH_2CH_2Ar$), 2.24 (m, 3.0H, $SiCH(CH_3)Ar$), 1.39 (m, 9.0H, $SiCH(CH_3)Ar$), 0.93 (m, 6.0H, $SiCH_2CH_2Ar$), 0.12 (m, 315H, $SiCH_3$).

EXAMPLE 3

Trimethylpyrimidinium-substituted silicone polymer ($MD_{48}D^{R2}_{3}M$). To a 500 milliliter round bottom flask containing a stir bar was added 151.2 g (36.543 mmol) of the benzylchloride-substituted silicone polymer $MD_{45}D^{R1}_{3}M$. Sodium iodide (15.30 grams, 102.1 millimoles) was added as a solid with 200 milliliters of acetone. This mixture was allowed to stir while 15.69 grams (101.7 millimoles) of 1,4,6-trimethylpyrimidine-2-thione were added in portions as a solid. An additional 300 milliliters of acetone was then added to the pale yellow reaction mixture which was allowed to stir for 24 hours at room temperature. After this time, the reaction mixture was vacuum filtered to remove solids. The volatile materials were removed from the filtrate under vacuum. The final product was isolated in 98.7% yield (163.2 grams) as a clear, light yellow, rubbery solid. $^{1}$H NMR (acetone-$d_6$): δ 7.91 (s, 3.0 H, pyH), 7.47 (m, 6.0 H, phenyl), 7.21 (m, 6.0 H, phenyl), 4.73 (s, 6.0 H, $CH_2S$), 4.14 (s, 9.0 H, $NCH_3$), 2.95 (s, 9.0 H, 6-aryl$CH_3$), 2.75 (s, 9.0 H, 4-aryl$CH_3$), 2.71 (m, 6.0 H, $SiCH_2CH_2$), 2.22 (m, 3.0 H, $SiCH(CH_3)$), 1.39 (d, 9.0 H, $SiCH(CH_3)$), 0.93 (m, 9.0 H, $SiCH_2CH_2Ar$), 0.12 (s, 315 H, $SiCH_3$).

EXAMPLE 4

1,1,3,3-Tetramethyl-2-thiuronium-substituted silicone polymer ($M^{R3}D_{46}M^{R3}$). The terminally substituted hydride fluid $M^{H}D_{46}M^{H}$ was prepared by the same method as described above for $MD_{48}D^{H}_{3}M$. To a 1 liter round bottom flask containing a stir bar was added 152.4 grams (38.09 millimoles) of the benzylchloride-substituted silicone $M^{R1}D_{46}M^{R1}$ prepared as described above for $MD_{48}D^{R1}_{3}M$. Sodium iodide (10.62 grams, 70.82 millimoles) was added as a solid with 200 milliliters of acetone. This mixture was allowed to stir while 9.380 grams (70.97 millimoles) of 1,1,3,3-tetramethyl-2-thiourea were added in portions as a solid. An additional 300 milliliters of acetone was then added to the pale yellow reaction mixture which was allowed to stir at room temperature for 3 days. After this time, the reaction mixture was vacuum filtered to remove solids and concentrated under vacuum almost to dryness.

The concentrated solution was then precipitated/washed three times with approximately 3 volume-equivalents of water in a blender. The resulting moist powder was dried under a nitrogen flow for 3 days. The final product was a light yellow powder, dispersed in a clear, golden yellow, slightly sticky rubber. 167.2 grams of polymer were isolated, a 92% yield of the dry polymer which contained 6.3 wt % water. $^1$H NMR (acetone-$d_6$): δ 7.43 (t, 4.0 H, phenyl), 7.23 (d, 4.0 H, phenyl), 7.14 (d, 4.0 H, phenyl), 4.51 (s, 4.0 H, CH$_2$S), 3.42 (s, 24.0 H, N(CH$_3$)$_2$), 2.69 (m, 4.0 H, SiCH$_2$CH$_2$), 2.25 (m, 2.0 H, SiCH(CH$_3$)), 1.37 (d, 6.0 H, SiCH(CH$_3$)), 0.93 (m, 4.0 H, SiCH$_2$CH$_2$Ar), 0.12 (s, 288 H, SiCH$_3$).

It should be noted that while most reactions in which cationic polymers were made were performed at room temperature, in most instances they can be heated to speed the reaction.

EXAMPLE 5–14

Using the same procedures as described above for the structurally analogous polymers, the following materials were also synthesized:

$M^{R3}D_{107}M^{R3}$
$M^{R3}D_{46}M^{R3}$
$MD_{47}D^{R4}_1M$
$MD_{55}D^{R4}_2M$
$M^{R4}D_{117}M^{R4}$
$M^{R4}D_{48}M^{R4}$
$M^{R4}D_{202}M^{R4}$
$M^{R4}D_{22}M^{R4}$
$M^{R4}D_7M^{R4}$
$MD_{45}D^{R4}_3M$

Silicone deposition. Polymers described in this invention impart durable benefits to hair such as good combability, manageability, etc. with significantly less buildup upon repeated applications when compared to polymers with a higher number of molecular hooks. The degree to which the new silicone materials interact with hair durably, after multi-shampoo with a commercially available shampoo (Prell®) and reapplication cycles, was measured. After a certain number of treatments (see Table 1), hair switches were analyzed for silicon by x-ray fluorescence (XRF). The counts were converted to parts per million (ppm) silicon deposition using standard methods.

TABLE 1.

XRF data collected on hair switches treated with new silicone polymers after extraction and 20 shampoos with Prell ®.

| Switches | Polymer | Number of treatment cycles | Silicon Deposition (ppm)[1] |
|---|---|---|---|
| 1–3 | MD$_{45}$D$^{R4}_3$M | 1 | 1567 |
| 4–6 | MD$_{45}$D$_3^{R4}$M | 2 | 1940 |
| 7–9 | MD$_{45}$D$_3^{R4}$M | 3 | 2187 |
| 10–12 | MD$_{45}$D$_3^{R4}$M | 5 | 4636 |
| 13–15 | MD$_{45}$D$_3^{R4}$M | 10 | 8960 |
| 16–18 | M$^{R4}$D$_{48}$M$^{R4}$ | 1 | 250 |
| 19–21 | M$^{R4}$D$_{48}$M$^{R4}$ | 2 | 301 |
| 22–24 | M$^{R4}$D$_{48}$M$^{R4}$ | 3 | 431 |
| 25–27 | M$^{R4}$D$_{48}$M$^{R4}$ | 5 | 377 |
| 28–30 | M$^{R4}$D$_{48}$M$^{R4}$ | 10 | 749 |

[1]Reported values are the average of measurements taken on three different hair switches treated under the same conditions.

Control experiments of hair switches treated with a polysiloxane without the linker and molecular hook (polydimethylsiloxane with a viscosity of 350 centistokes) for 5 minutes showed an initial deposition level of silicon as 2050 parts per million by XRF. Measurements showed that after 8 shampoos, no silicone remained on the hair. The data in Table 1 clearly show that both disubstituted polymer $M^{R4}D_{48}M^{R4}$ and trisubstituted polymer $MD_{45}D^{R4}_3M$, which provide conditioning benefits, do adhere to the hair with unexpected durability as compared to the control experiments. The data also show, surprisingly, that the disubstituted polymer $M^{R4}D_{48}M^{R4}$ results in significantly less buildup than the trisubstituted polymer $MD_{45}D^{R4}_3M$. Note that the degree of polymerization is the same for both of these polymers. Over the course of 10 application cycles, the amount of silicone on the hair increased 6-fold for the trisubstituted polymer, but only 3-fold for the disubstituted polymer. Therefore in both cases, durability is observed, however polymers with 2 or fewer hooks lead to less buildup. This is a clear advantage considering repeated consumer use over long periods of time.

While typical embodiments have been set forth for the purpose of illustration, the foregoing description should not be deemed to be a limitation on the scope of the invention. Accordingly, various modifications, adaptations, and alternatives may occur to one skilled in the art without departing from the spirit and scope of the present invention.

What is claimed is:

1. A silicone composition which comprises at least one polysiloxane or silicone resin containing at least one linker, and one or two molecular hooks.

2. The composition in accordance with claim 1, wherein the at least one linker is bound to a polysiloxane or silicone resin through a silicon, carbon, oxygen, nitrogen, or sulfur atom.

3. The composition in accordance with claim 2, wherein the at least one linker is bound to a polysiloxane or silicone resin through a silicon atom.

4. The composition in accordance with claim 1 having the formula $$M_a M'_b D_c D'_d T_e T'_f Q_g$$

where the subscripts a, b, c, d, e, f and g are zero or a positive integer, subject to the limitation that the sum of the subscripts b, d and f is one or two; where M has the formula:

$R^{34}_3SiO_{1/2}$,

M' has the formula:

$(Z-Y)R^{35}_2SiO_{1/2}$,

D has the formula:

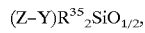

$R^{36}_2SiO_{2/2}$,

D' has the formula:

$(Z-Y)R^{37}SiO_{2/2}$,

T has the formula:

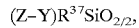

$R^{38}SiO_{3/2}$,

T' has the formula:

$(Z-Y)SiO_{3/2}$,

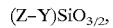

and Q has the formula $SiO_{4/2}$, where each $R^{34}$, $R^{35}$, $R^{36}$, $R^{37}$, $R^{38}$ is independently at each occurrence a hydrogen atom, $C_{1-22}$ alkyl, $C_{1-22}$ alkoxy, $C_{2-22}$ alkenyl, $C_{6-14}$ aryl, $C_{6-22}$ alkyl-substituted aryl, $C_{6-22}$ aralkyl, $C_{1-22}$ fluoroalkyl, $C_{1-22}$ polyether, or $C_{1-22}$ amino alkyl; each Z, independently at each occurrence, is a molecular hook; and each Y, independently at each occurrence, is a linker.

5. The composition of claim 4 comprising at least one compound of the following formulas, (I), (II), (III), (IV), (V), or (VI):

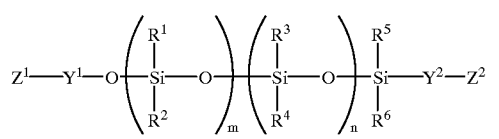

(I)

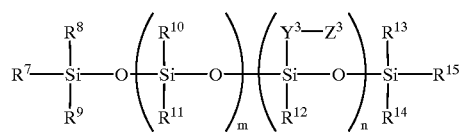

(II)

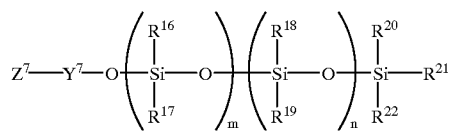

(III)

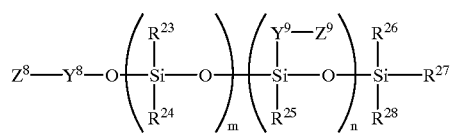

(IV)

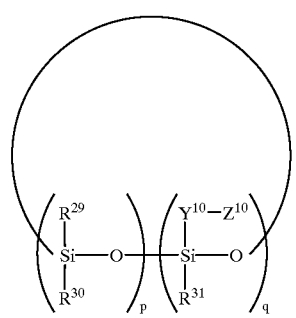

(V)

$(R^{32}{}_3SiO_{1/2})_a[(Z-Y)R^{33}{}_2SiO_{1/2}]_b(SiO_{4/2})_g$  (VI)

where each $R^{1-33}$ is independently at each occurrence a hydrogen atom, $C_{1-22}$ alkyl, $C_{1-22}$ alkoxy, $C_{2-22}$ alkenyl, $C_{6-14}$ aryl, $C_{6-22}$ alkyl-substituted aryl, $C_{6-22}$ aralkyl, fluoroalkyl; Z, $Z^{1-3}$, and $Z^{7-10}$, independently at each occurrence, is a molecular hook; and Y, $Y^{1-3}$, and $Y^{7-10}$, independently at each occurrence, is a linker; wherein "m" in each formula has a value in a range between about 0 and about 26,000; "n" in each formula has a value in a range between about 0 and about 2 with the proviso that in formula (II) "n" is not 0; "m+n" in each formula has a value in a range between about 1 and about 26,000; "q" has a value of one or two; "p+q" has a value of at least 3; "a" has a value greater than or equal to one; and "b" and "g" have a value of at least one.

6. The composition in accordance with claim 5 comprising at least one compound of formulas (I), (II), (III), or (IV) wherein $R^{1-28}$ is methyl; "m" in each formula has a value in a range between about 15 and about 120; and "m+n" in each formula has a value in a range between about 15 and about 120.

7. The composition in accordance with claim 5 comprising at least one compound of formula (V), wherein "p+q" has a value in a range between about 3 and about 6; and $R^{29-31}$ is methyl.

8. The composition in accordance with claim 5, wherein the moiety Z-Y is prepared by a process which comprises combining a hook with a linker precursor comprising a linker and a leaving group.

9. The composition in accordance with claim 8, wherein the leaving group is selected from the group consisting of chloride, bromide, iodide, tosylate, mesylate, phosphate, and cyclic leaving groups containing at least one heteroatom.

10. The composition in accordance with claim 9, wherein the leaving group is iodide, chloride, or bromide.

11. The composition in accordance with claim 1, wherein the molecular hook comprises a heterocyclic pyridinium compound, a heterocyclic triazinium compound, a heterocyclic pyrimidinium compound, or a heterocyclic pyrazine compound.

12. The composition in accordance with claim 11, wherein the molecular hook is at least one member selected from the group consisting of a heterocyclic pyridinium compound (VII), a heterocyclic triazinium (VI), a heterocyclic pyrimidinium compound (IX), and a heterocyclic pyrazine compound (X):

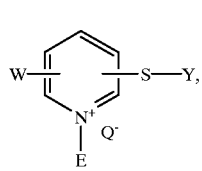

(VII)

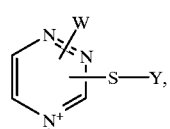

(VIII)

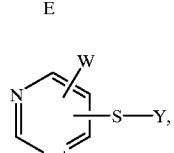

(IX)

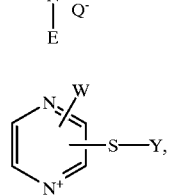

(X)

wherein Y is a linker; W is hydrogen or is selected from electron withdrawing, electron neutral, or electron donating groups with Hammett sigma para values between −1.0 and +1.5 comprising carbonlinked groups of the classes defined as $E^1$, $E^2$, $E^3$, and $E^4$; S-linked groups including $SE^1$, SCN, $SO_2E^1$, $SO_3E^1$, $SSE^1$, $SOE^1$, $SO_2NE^1E^2$, $SNE^1E^2$, $S(NE^1)E^2$, $SE^1$ ($NE^2$), $SONE^1E^2$; O-linked groups including $OE^1$, OCN, ONE¹E²; N-linked groups including NE¹E², NE¹E²E³⁺, NE¹OE², NE¹SE², NCO, NCS, NO₂, N=NE¹, N=NOE¹, NE¹CN, N=C=NE¹, NE¹NE²E³, NE¹NA²NA³A⁴, NA¹N=NE²; other groups including CONE¹₂, CONE¹COE², C(=NE¹)NE¹E², CHO, CHS, CN, NC, Hal, and derived groups that connect one or more of the optional substituents via a ring system; Hal is fluorine, chlorine, bromine, or iodine; and wherein B, E¹, E², E³, and E⁴ each represent, independently from one another, a monovalent group which can be silicone group, H, or any of the following: a straight, branched or mono- or polycyclic aliphatic, mono- or polyunsaturated alkyl, aryl, heteroalkyl, heteroaliphatic or heteroolefinic system including carbon atoms in a range between about 1 and about 30 together with heteroatoms in a range between about 0 and about 15, including oxygen, nitrogen, sulfur, phosphorus, silicon and incorporating one or more substituents including mono, poly or perfluoro substitution; and wherein the counterion, Q⁻, is selected from the group consisting of halides, borates, phosphates, tosylates, mesylates, and triflates.

13. The composition in accordance with claim 1, wherein the linker comprises a C₁–C₁₀₀ alkyl, aryl, or alkylaryl group optionally containing one or more heteroatoms.

14. The composition in accordance with claim 13, wherein the linker comprises at least one compound of the formula (XI), (XII), (XIII), (XIV), (XV), (XVI), or (XVII):

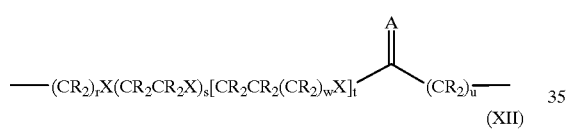
(XI)

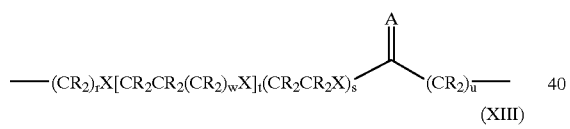
(XII)

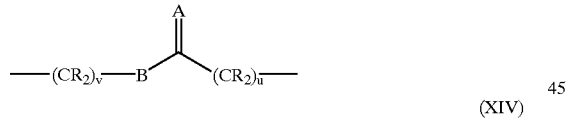
(XIII)

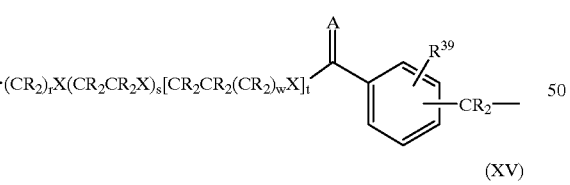
(XIV)

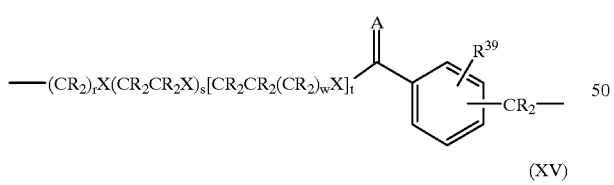
(XV)

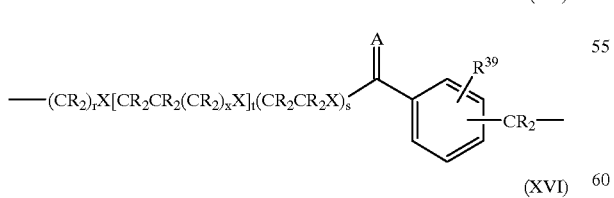
(XVI)

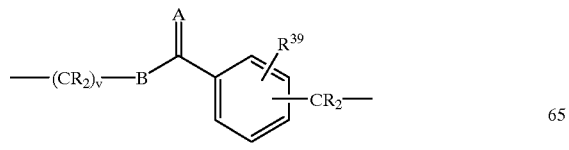
(XVII)

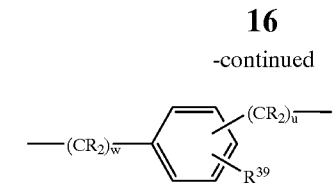

where
- r is in a range between about 1 and about 10;
- s is in a range between about 0 and about 100;
- t is in a range between about 0 and about 100;
- u is in a range between about 1 and about 10;
- v is in a range between about 1 and about 10;
- w is 1 or 2;
- x is 1 or 2;
- X is O, NOH, NOR, or NR;
- wherein R is independently at each occurrence hydrogen (H), C₁₋₂₂ alkyl, C₁₋₂₂ alkoxy, C₂₋₂₂ alkenyl, C₆₋₁₄ aryl, C₆₋₂₂ alkyl-substituted aryl, or C₆₋₂₂ aralkyl where the C can be unsubstituted or substituted with heteroatoms such as oxygen (O), nitrogen (N), sulfur (S) or halogen;
- wherein R³⁹ is independently at each occurrence hydrogen (H), C₁₋₂₂ alkyl, C₁₋₂₂ alkoxy, C₂₋₂₂ alkenyl, C₆₋₁₄ aryl, C₆₋₂₂ alkyl-substituted aryl, C₆₋₂₂ aralkyl, or fused ring system which may or may not be fused to the phenyl group where the C can be unsubstituted or substituted with heteroatoms such as O, N, S or halogen;
- A is O, NOH, NOR, NR or S;
- B is O, NOH, NOR, NR or S; and
- where the polysiloxane or the silicone resin is bound to the (CR₂)ᵣ (Formula XI, XII, XIV, and XV), (CR₂)ᵥ (Formula XIII and XVI), or (CR₂)ᵥᵥ (Formula XVII).

15. The composition in accordance with claim 14, wherein r is 2 or 3; s is in a range between about 4 and about 20; t is 0; u is 1; v is 2 or 3; w is 1 or 2; x is 1 or 2; X is O; R is H; R³⁹ is H; A is O; and B is O.

16. A hair care product comprising the composition of claim 1.

17. A textile care product comprising the composition of claim 1.

18. A cosmetic product comprising the composition of claim 1.

19. An oral care product comprising the composition of claim 1.

20. An animal care product comprising the composition of claim 1.

21. A method for providing adhesion of polysiloxane or silicone resin to hair which comprises treating hair with the composition of claim 1.

22. A silicone composition comprising at least one compound of the formula

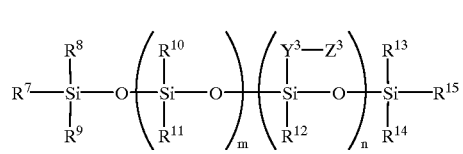
(II)

where each R⁷⁻¹⁵ is methyl; Z³ is a pyrimidinium molecular hook of the formula (IX)

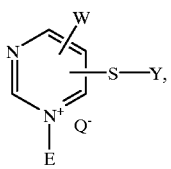

(IX)

wherein W is hydrogen, E is methyl; Q is iodide; and Y is at least one compound of the formulas (XI), (XII), (XIII), (XIV), (XV), (XVI), or (XVII):

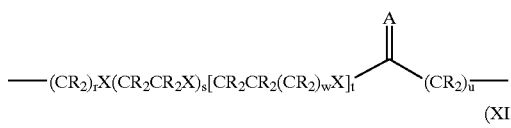

(XI)

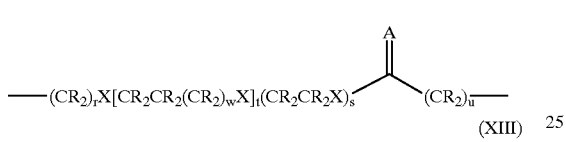

(XII)

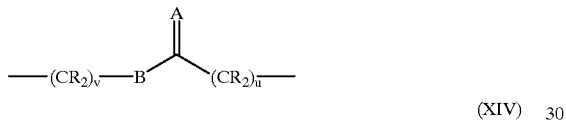

(XIII)

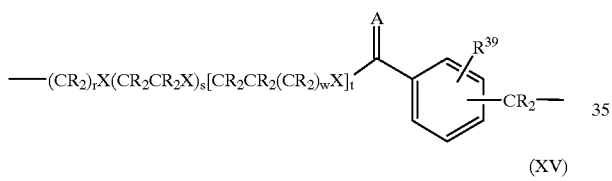

(XIV)

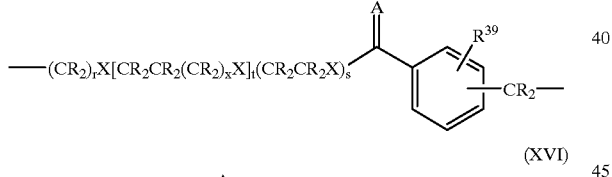

(XV)

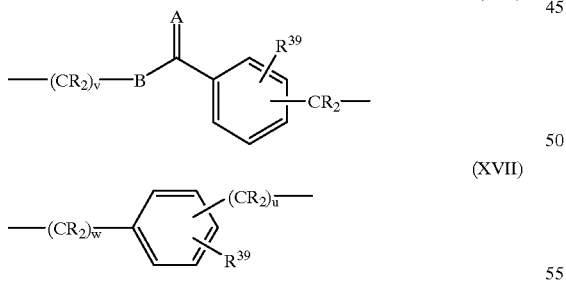

(XVI)

(XVII)

wherein "m" has a value in a range between about 15 and about 120; "n" is 1 or 2; r is 2 or 3; s is in a range between about 4 and about 20; t is 0; u is 1; v is 2 or 3; w is 1 or 2; x is 1 or 2; X is O; R is H; $R^{39}$ is H; A is O; B is O; and where the polysiloxane is bound to the $(CR_2)_r$ (Formula XI, XII, XIV, and XV), $(CR_2)_v$ (Formula XIII and XVI), or $(CR_2)_w$ (Formula XVII).

23. A hair care product comprising the composition of claim 22.

24. A method for providing adhesion of polysiloxane to hair which comprises treating hair with the composition of claim 22.

25. A silicone composition comprising at least one compound of the formula (I):

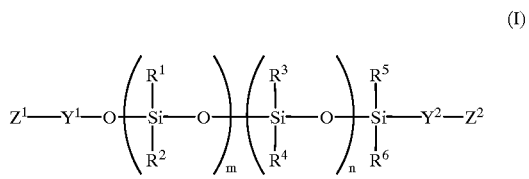

(I)

where each $R^{1-6}$ is methyl; $Z^{1-2}$ are each a pyrimidinium molecular hook of the formula (IX):

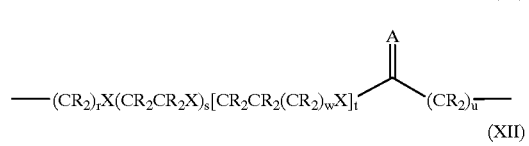

(IX)

wherein W is hydrogen, E is methyl; Q is iodide, chloride, or bromide; and Y is at least one compound of the formulas (XI), (XII), (XIII), (XIV), (XV), (XVI), or (XVII):

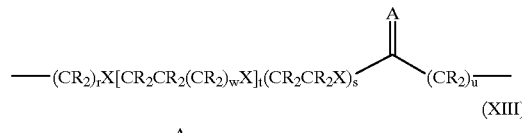

(XI)

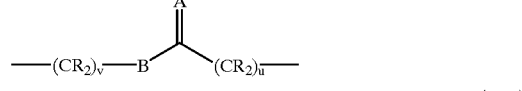

(XII)

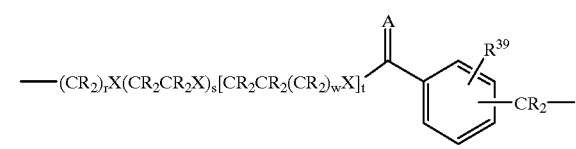

(XIII)

(XIV)

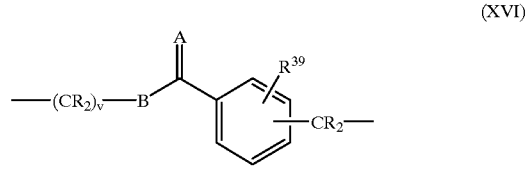

(XV)

(XVI)

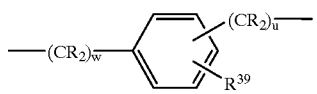

(XVII)

wherein "m+n" has a value in a range between about 15 and about 120; r is 2 or 3; s is in a range between about 4 and about 20; t is 0; u is 1; v is 2 or 3; w is 1 or 2; x is 1 or 2; X is O; R is H; $R^{39}$ is H; A is O; B is O; and where the polysiloxane is bound to the $(CR_2)_r$ (Formula XI, XII, XIV, and XV), $(CR_2)_v$ (Formula XIII and XVI), or $(CR_2)_w$ (Formula XVII).

26. A hair care product comprising the composition of claim 25.

27. A method for providing adhesion of polysiloxane to hair which comprises treating hair with the composition of claim 25.

28. A method for making a silicone composition comprising at least one polysiloxane or silicone resin, at least one linker, and either one or two molecular hooks, which method comprises combining a linker, a molecular hook and a polysiloxane or silicone resin.

29. The method of claim 28 which comprises combining at least one linker with a polysiloxane or silicone resin and subsequently combining said combination with either one or two molecular hooks.

30. The method of claim 28 which comprises combining at least one linker with either one or two molecular hooks and subsequently combining said combination with a polysiloxane or silicone resin.

31. The method of claim 28 in which the at least one linker is bound to a polysiloxane or silicone resin through a silicon, carbon, oxygen, nitrogen, or sulfur atom.

32. The method of claim 31 in which the at least one linker is bound to a polysiloxane or silicone resin through a silicon atom.

33. The method of claim 28 in which the at least one polysiloxane or silicone resin comprises at least one compound of the following formulas, (I), (II), (III), (IV), (V), or (VI):

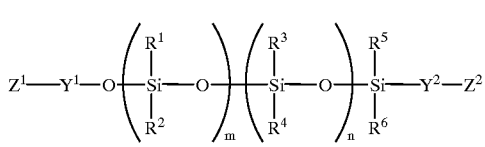

(I)

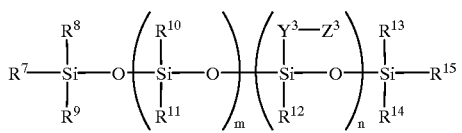

(II)

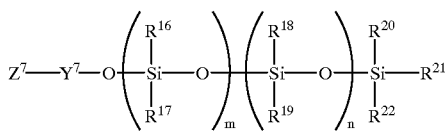

(III)

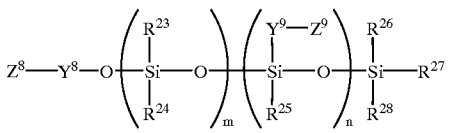

(IV)

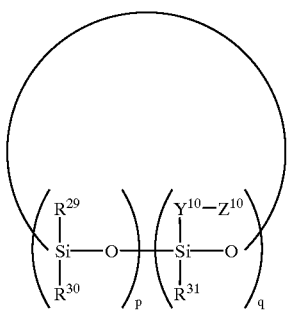

(V)

$(R^{32}{}_3SiO_{1/2})_a[(Z-Y)R^{33}{}_2SiO_{1/2}]_b(SiO_{4/2})_g$ (VI)

where each $R^{1-33}$ is independently at each occurrence a hydrogen atom, $C_{1-22}$ alkyl, $C_{1-22}$ alkoxy, $C_{2-22}$ alkenyl, $C_{6-14}$ aryl, and $C_{6-22}$ alkyl-substituted aryl, $C_{6-22}$ aralkyl, and $C_{1-22}$ fluoroalkyl; $Z^{1-10}$, independently at each occurrence, is a molecular hook; and $Y^{1-10}$, independently at each occurrence, is a linker; wherein "m" in each formula has a value in a range between about 0 and about 26,000; "n" in each formula has a value in a range between about 0 and about 2 with the proviso that in formula (II) "n" is not 0; "m+n" in each formula has a value in a range between about 1 and about 26,000; "q" has a value one or two; "p+q" has a value of at least 3; "a" has a value greater than or equal to one; and "b" and "g" have a value of at least one.

34. The method of claim 33, wherein the polysiloxane comprises at least one compound of the formula (I), (II), (III), or (IV) wherein $R^{1-28}$ is methyl; "m" in each formula has a value in a range between about 15 and about 120; and "m+n" in each formula has a value in a range between about 15 and about 120.

35. The method of claim 33, wherein the polysiloxane comprises at least one compound of formula (V) wherein "p+q" has a value in a range between about 3 and about 6; and $R^{29-31}$ is methyl.

36. The method of claim 33, wherein the moiety Z-Y is prepared by a process which comprises combining a hook with a linker precursor comprising a linker and a leaving group.

37. The method of claim 36, wherein the leaving group is selected from the group consisting of chloride, bromide, iodide, tosylate, mesylate, phosphate, and cyclic leaving groups containing at least one heteroatom.

38. The method of claim 37, wherein the leaving group is iodide, chloride, or bromide.

39. The method of claim 28, wherein the molecular hook comprises a heterocyclic pyridinium compound, a heterocyclic triazinium compound, a heterocyclic pyrimidinium compound, or a heterocyclic pyrazine compound.

40. The method of claim 39, wherein the molecular hook is at least one member selected from the group consisting of a heterocyclic pyridinium compound (VII), a heterocyclic triazinium compound (VIII), a heterocyclic pyrimidinium compound (IX), and a heterocyclic pyrazine compound (X):

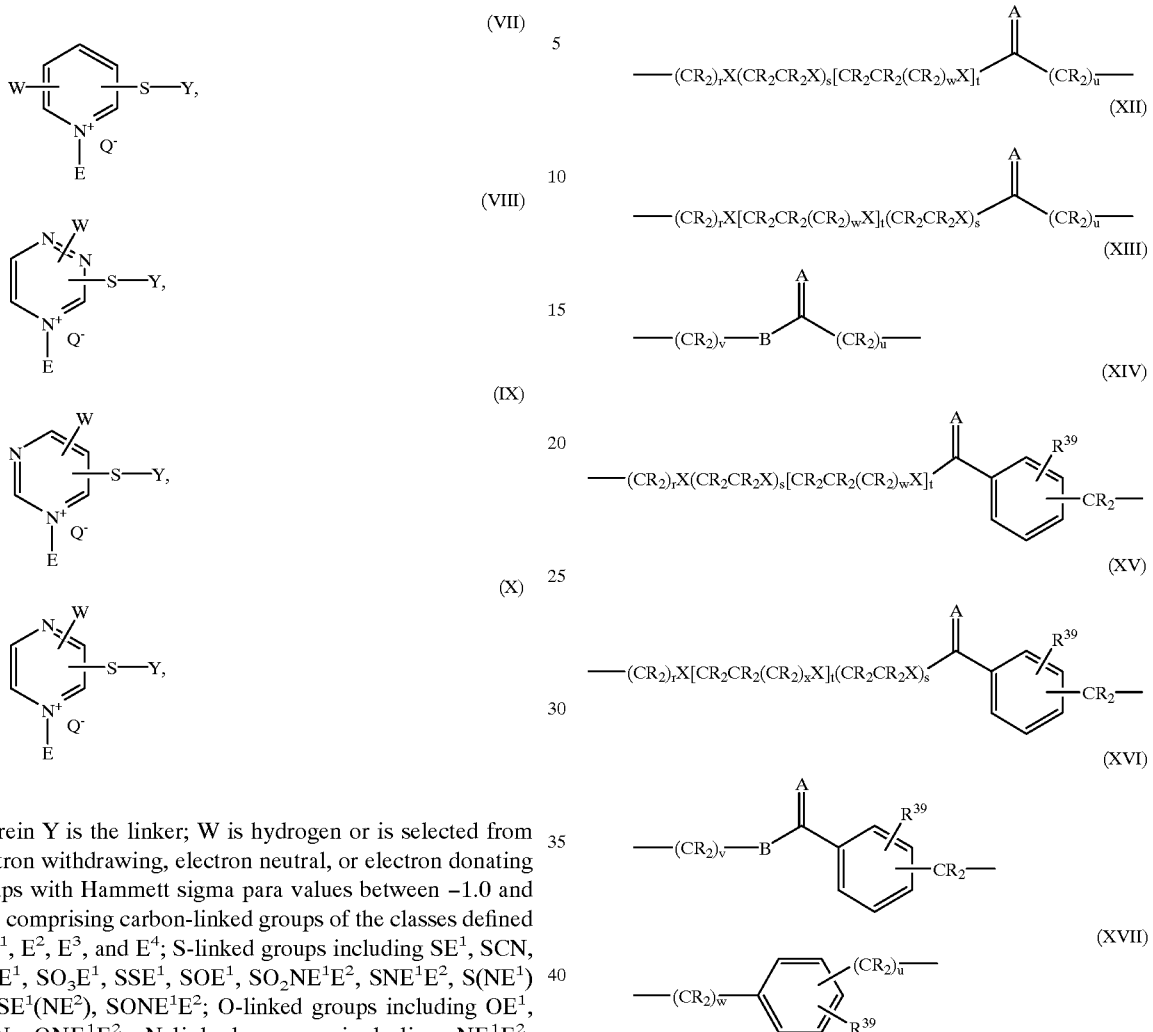

wherein Y is the linker; W is hydrogen or is selected from electron withdrawing, electron neutral, or electron donating groups with Hammett sigma para values between −1.0 and +1.5 comprising carbon-linked groups of the classes defined as $E^1$, $E^2$, $E^3$, and $E^4$; S-linked groups including $SE^1$, SCN, $SO_2E^1$, $SO_3E^1$, $SSE^1$, $SOE^1$, $SO_2NE^1E^2$, $SNE^1E^2$, $S(NE^1)E^2$, $SE^1(NE^2)$, $SONE^1E^2$; O-linked groups including $OE^1$, OCN, $ONE^1E^2$; N-linked groups including $NE^1E^2$, $NE^1E^2E^{3+}$, $NE^1OE^2$, $NE^1SE^2$, NCO, NCS, $NO_2$, $N=NA^1$, $N=NOE^1$, $NE^1CN$, $N=C=NE^1$, $NE^1NE^2E^3$, $NE^1NE^2NE^3E^4$, $NE^1N=NE^2$; other groups including $CONE^1_2$, $CONE^1COE^2$, $C(=NE^1)NE^1E^2$, CHO, CHS, CN, NC, Hal, and derived groups that connect one or more of the optional substituents via a ring system; Hal is fluorine, chlorine, bromine, or iodine; and wherein E, $E^1$, $E^2$, $E^3$, and $E^4$ each represent, independently from one another, a monovalent group which can be the group, R, or H or any of the following: a straight, branched or mono- or polycyclic aliphatic, mono- or polyunsaturated alkyl, aryl, heteroalkyl, heteroaliphatic or heteroolefinic system including carbon atoms in a range between about 1 and about 30 together with heteroatoms in a range between about 0 and about 15, including oxygen, nitrogen, sulfur, phosphorus, silicon and incorporating one or more substituents including mono, poly or perfluoro substitution; and wherein the counterion, $Q^−$, is selected from the group consisting of halides, borates, phosphates, tosylates, mesylates, and triflates.

41. The method in accordance with claim 28, wherein the linker comprises at least one compound of the formula (XI), (XII), (XIII), (XIV), (XV), (XVI), or (XVII):

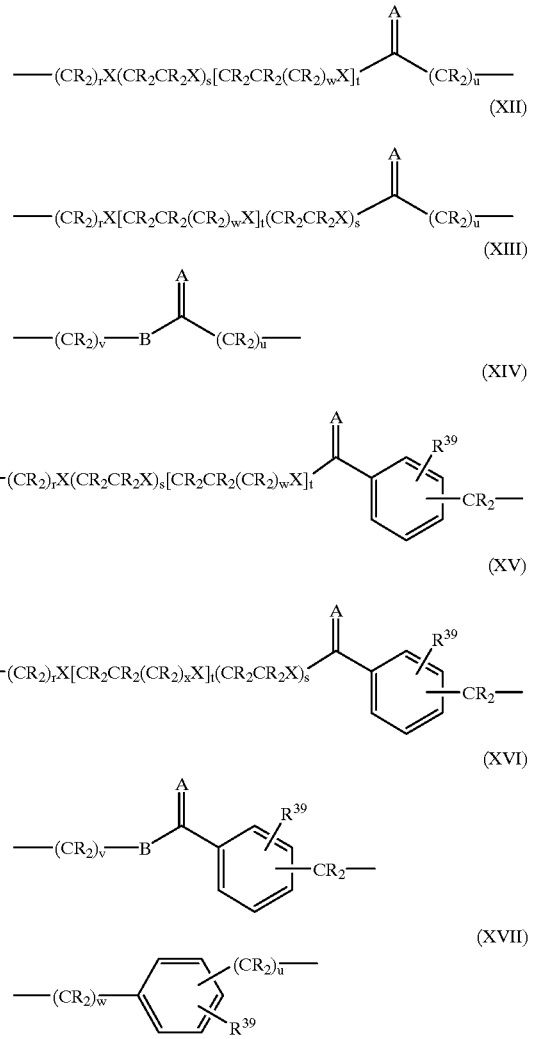

where
r is in a range between about 1 and about 10;
s is in a range between about 0 and about 100;
t is in a range between about 0 and about 100;
u is in a range between about 1 and about 10;
v is in a range between about 1 and about 10;
w is 1 or 2;
x is 1 or 2;
X is O, NOH, NOR or NR;
wherein R is independently at each occurrence hydrogen (H), $C_{1-22}$ alkyl, $C_{1-22}$ alkoxy, $C_{2-22}$ alkenyl, $C_{6-14}$ aryl, and $C_{6-22}$ alkyl-substituted aryl, and $C_{6-22}$ aralkyl where the C can be unsubstituted or substituted with heteroatoms such as oxygen (O), nitrogen (N), sulfur (S) or halogen;
wherein $R^{39}$ is independently at each occurrence hydrogen (H), $C_{1-22}$ alkyl, $C_{1-22}$ alkoxy, $C_{2-22}$ alkenyl, $C_{6-14}$ aryl, $C_{6-22}$ alkyl-substituted aryl, $C_{6-22}$ aralkyl, and fused ring system which may or may not be fused to the phenyl group where the C can be unsubstituted or substituted with heteroatoms such as O, N, S or halogen;
A is O, NOH, NOR, NR or S;
B is O, NOH, NOR, NR or S; and where the polysiloxane or the silicone resin is bound to the $(CR_2)_r$ (Formula XI, XII, XIV, and XV), $(CR_2)_v$ (Formula XIII and XVI), or $(CR_2)_w$ (Formula XVII).

42. The method in accordance with claim 41, wherein r is 2 or 3; s is in a range between about 4 and about 20; t is 0; u is 1; v is 2 or 3; w is 1 or 2; x is 1 or 2; X is O; R is H; $R^{39}$ is H; A is O; and B is O.

43. A method for making a silicone composition comprising combining at least one linker with a polysiloxane and subsequently combining said combination with at least one molecular hook, wherein the polysiloxane comprises a compound of the formula (II):

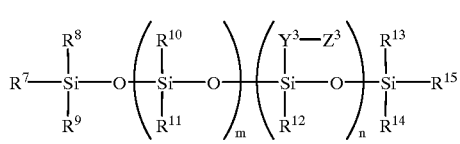
(II)

where each $R^{7-15}$ is methyl; $Z^3$ is a pyrimidinium molecular hook of the formula (IX)

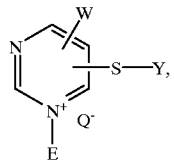
(IX)

wherein W is hydrogen, E is methyl; Q is iodide; and Y is at least one compound of the formulas (XI), (XII), (XIII), (XIV), (XV), (XVI), or (XVII):

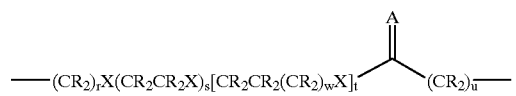
(XI)

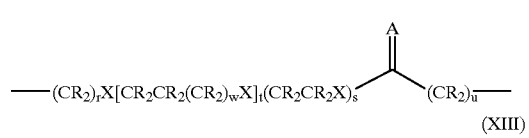
(XII)

(XIII)

(XIV)

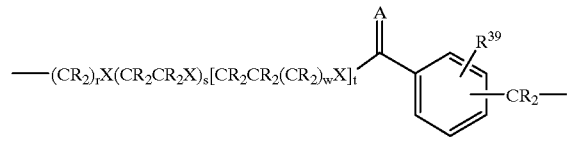

-continued

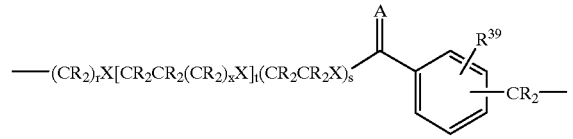
(XV)

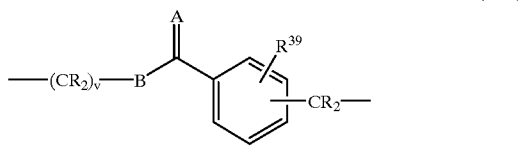
(XVI)

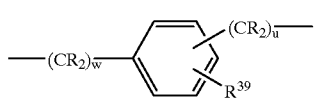
(XVII)

wherein "m" is in a range between about 15 and about 120; "n" is 1 or 2; r is 2 or 3; s is in a range between about 4 and about 20; t is 0; u is 1; v is 2 or 3; w is 1 or 2; x is 1 or 2; X is O; R is H; $R^{39}$ is H; A is O; B is O; and where the polysiloxane is bound to the $(CR_2)_r$ (Formula XI, XII, XIV, and XV), $(CR_2)_v$ (Formula XIII and XVI), or $(CR_2)_w$ (Formula XVII).

44. A method for making a silicone composition comprising combining at least one linker with a polysiloxane and subsequently combining said combination with at least one molecular hook, wherein the polysiloxane comprises a compound of the formula (I):

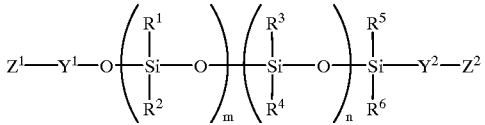
(I)

where each $R^{1-6}$ is methyl; $Z^{1-2}$ are each a pyrimidinium molecular hook of the formula (IX):

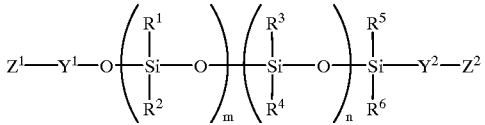
(IX)

wherein W is hydrogen, E is methyl; Q is iodide, chloride, or bromide; and Y is at least one compound of the formulas (XI), (XII), (XIII), (XIV), (XV), (XVI), or (XVII):

(XI)

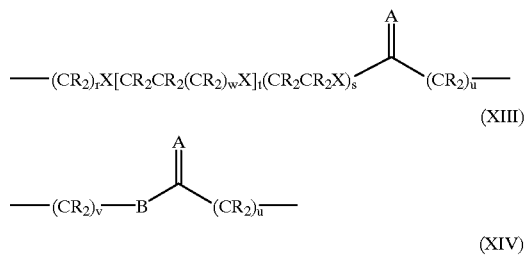
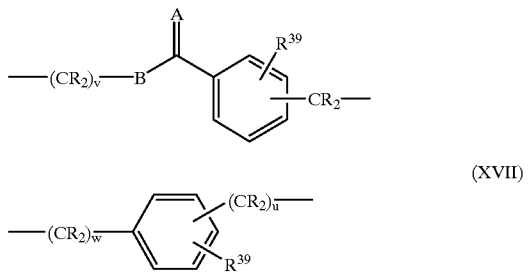
wherein "m+n" has a value in a range between about 15 and about 120; r is 2 or 3; s is in a range between about 4 and about 20; t is 0; u is 1; v is 2 or 3; w is 1 or 2; x is 1 or 2; X is O; R is H; $R^{39}$ is H; A is O; B is O; and where the polysiloxane is bound to the $(CR_2)_r$ (Formula XI, XII, XIV, and XV), $(CR_2)_v$ (Formula XIII and XVI), or $(CR_2)_w$ (Formula XVII).
* * * * *